United States Patent [19]
Hirai et al.

[11] Patent Number: 5,694,196
[45] Date of Patent: Dec. 2, 1997

[54] EXPERIMENTAL INSTRUMENT FOR EXAMINING PERMEABILITY OF A FLOWING CORNEA AND AN EXPERIMENTAL UNIT USING SAID EXPERIMENTAL INSTRUMENT

[75] Inventors: Yoshiaki Hirai, Fukuoka; Kakuji Tojo, 781-304, Kobukuro, Iizuka-shi, Fukuoka 820, both of Japan

[73] Assignees: Kakuji Tojo; Senju Seiyaku Kabushiki Kaisha, both of Osaka, Japan

[21] Appl. No.: 408,024

[22] Filed: Mar. 21, 1995

[30] Foreign Application Priority Data

Mar. 22, 1994 [JP] Japan ................... 6-050685

[51] Int. Cl.⁶ ................... A61B 3/00; F04B 17/00
[52] U.S. Cl. ................... 351/200; 351/247; 417/420
[58] Field of Search ................... 351/200, 212, 351/247; 417/420; 604/8

[56] References Cited

U.S. PATENT DOCUMENTS 5,599,175  2/1997  Tojo et al. ................... 417/420

FOREIGN PATENT DOCUMENTS

64-30434  2/1989  Japan.

Primary Examiner—Huy Mai
Attorney, Agent, or Firm—Seed and Berry LLP

[57] ABSTRACT

An experimental instrument for examining permeability of a flowing cornea is used for imitating a lacrimal layer in the front part of a cornea or the back part of the cornea (an aqueous humor) by means of storing a various kinds of solutions comprises a cell body including a stirring part of a cylindrical wall and a bottom surface at a bottom part thereof, a constant temperature tank which surrounds the cell body all around a sample membrane setting part which is protrusively arranged at an outer surface of the call body and can set a sample membrane such as a contact lens used as a cornea or a corneal model, an outflow tube which is protrusively arranged at an outer surface of the stirring part and makes a solution in the cell body discharge, an inflow tube which is protrusively arranged at an upper part of the cell body and makes the solution flow inside of the cell body, a magnet rotator which is arranged inside the stirring part of the cell body, and a magnet stirrer which makes the magnet rotator inside the cell body rotate by means of magnetic force.

8 Claims, 7 Drawing Sheets

EXPERIMENTAL INSTRUMENT FOR EXAMINING PERMEABILITY OF A FLOWING CORNEA AND AN EXPERIMENTAL UNIT USING SAID EXPERIMENTAL INSTRUMENT

BACKGROUND OF THE INVENTION

Detailed Description of the Invention

1. Field of the Invention

The present invention relates to an experimental instrument for examining permeability of a flowing cornea and an experimental unit using said experimental instrument for aiming at basic study in the medicinal behavior in the development of new medicine in the ophthalmology field.

2. Description of the Prior Art

As the experimental unit using for the experiments for examining permeability of a flowing cornea or the like, it is generally well-known that a donor cell to store lacrimal fluid containing medicines and to imitate a lacrimal layer in the front part of a cornea after applying eye drops to eyes is connected with a receptor cell to imitate the state of the back part of the cornea (an aqueous humor) through a sample membrane setting part (of Japanese JITSUYO SHINAN KOKAI No. 64-30434).

The clinical trials makes it clear that the medicinal density of the lacrimal fluid after applying eye drops to eyes are often diluted by the lacrimal fluid secreted by the lachrymal gland and is declined according to a linear and a quadratic speed formulas. It is also clear that a flow is about 3 μl/min in the aqueous humor which the medicines reach after flowing the cornea.

Conventionally, the experimental unit has been proposed, wherein both of the donor cell which imitates the state of the lacrimal layer in the front part of the cornea and the receptor cell which imitates the state of the back part of the cornea include respectively a solution flow means which can control a micro-flow such as so-called ironing pump. In other words, this experimental unit provides the lacrimal fluid which does not include the medicines by means of the ironing pump within the donor cell to store the medicinal lacrimal fluid, thereby making it possible to imitate the state to decline the density of medicines after applying eye drops to eyes. Moreover, the aqueous humor in the receptor cell for storing it is circulated by the ironing pump or the like, whereby the flow of the aqueous humor in the back part of the cornea can be imitated.

However, in the case of the above conventional experimental unit, using the ironing pump as the solution flow means causes to carry the solution to be fed through the inside of the elastic tube body by ironing the elastic tube body by roller or the like, whereby the ironing causes the solution to pulsate. In other words, in case of controlling the micro-flow, the influence of the pulsatory has too much increased to control the volume of the flow, thereby causing the inconvenience to make it impossible to imitate the behavior of the lacrimal fluid and the aqueous humor in the donor cell and the receptor cell. Therefore, it has been proposed to employ the ironing pump which controls the pulsatory by means of improvement of ironing state of the elastic tube body by the roller. However, it makes the organization of the pump complicated, whereby the pump itself will be expensive.

Furthermore, in case of carrying the solution which includes the medicines in a low density, the medicines of the solution are adsorbed to the elastic tube body or are dissolved in it with the result that the medicines are dissolved in the solution again, whereby the inconvenience causes that the measurement of the behavior of the medicines is incorrect or the like.

In addition, in case of the above conventional experimental unit, the pump is necessary at any cost in carrying the solution to the donor cell and the receptor cell. Therefore, the inconveniences happen that it is easy for the solution to be remained at the inside of the pump and the flowing way of the solution of the experimental unit itself becomes long thereby making it difficult to balance the inflow and outflow of the substances in the experimental data.

SUMMARY OF THE INVENTION

The present invention, taking the above circumstances into consideration, has an object to provide an experimental instrument for examining permeability of a flowing cornea and an experimental unit using said experimental instrument, whereby behavior of lacrimal fluid and an aqueous humor in applying the eye drops to eyes can be imitated much closer to the real state and the medicinal behavior can be clearly measured.

In order to solve the above problems, an experimental instrument for examining permeability of a flowing cornea according to the invention being suited for imitating a lacrimal layer in the front part of a cornea or the back part of the cornea (an aqueous humor) by means of storing a various kinds of solutions comprises a cell body including a stirring part of a cylindrical wall and a bottom surface at a bottom, part thereof, a constant temperature tank which surrounds the call body all around a sample membrane setting part which is protrusively arranged at an outer surface of the cell body and can set a sample membrane such as a contact lens used as a cornea or a corneal model, an outflow tube which is protrusively arranged at an outer surface of the stirring part and makes a solution in the cell body discharge, an inflow tube which is protrusively arranged at an upper part of the cell body and makes the solution flow inside of the cell body, a magnet rotator which is arranged inside the stirring part of the cell body, and a magnet stirrer which makes the magnet rotator inside the cell body rotate by means of magnetic force.

Moreover, the 2 sets of the experimental instruments are structually connected with each other through the sample membrane such as the contact lens as the cornea or the corneal model set between the sample membrane setting parts.

At the stirring part in the cell body, making the magnet rotator rotate can occur the continuous swirling flow by which the solution stored in the call body can be discharged from the outflow tube. According to this, the new solution is fed from the inflow tube, which can make the density of the solution in the cell body change. Moreover, the inflow tube is connected to the outflow tube, thereby enabling the solution in the cell body to be circulated repeatedly. At this time, the number of revolution of the magnet rotator is changed to control the swirling flow, thereby enabling the solution in the cell body to be changed the density and circulated according to the desired the zero-degree, the linear or the quadratic speed formula. The density change and circulation of solution are achieved by rotation of the magnet rotator by means of the magnetic force, thereby enabling the whole of the present invention to be formed by heat resisting and chemical resisting material without being influenced by absorption or dissolution of the solution.

One cell body which is connected with the other via the sample membrane is employed as the donor cell which imitates the state of the back part of the cornea (the aqueous humor), the other cell body is used as the receptor which imitates the state of the lacrimal layer in the front part of the cornea, thereby making it possible to reproduce all actions which happen around the cornea.

As is described above, the present invention enables the solution in the cell body to be diluted according to the desired zero-degree, linear and quadratic speed formulas or to be circulated at the desired speed, thereby making it possible to imitate the state of the lacrimal fluid in the lacrimal layer of the front part of the cornea and the state of the aqueous humor of the back part of the cornea much closer to reality.

The cell body can be made of heat resisting and chemical resisting glass and the magnet rotator can be covered with heat resisting and chemical resisting resin, thereby preventing the solution from being influenced by absorption or dissolution of the liquid and achieving an accurate experiment which has only a smallest error.

The present invention enables the solution to be fed and circulated without using pump, thereby preventing the solution from remaining at the inner part of the pump and preventing the balance of errors of the experimental data from increasing as the result of lengthening the flowing way of the solution.

In addition, it is needless to use pump and the flowing way may be short, leading to convenience. Therefore, in constructing the experimental unit, a various kinds of experimental units such as open type, close circulation type, open circulation types can be devised, thereby achieving a wide scope of experiment at arbitrary.

BRIEF DESCRIPTION OF THE DRAWINGS

FIGS. 1(a–b) are a cross-sectional view and a sectional side elevation exemplarily illustrating a general structure of an experimental instrument for examining permeability of a flowing cornea according to the present invention.

DETAILED DESCRIPTION OF THE PREFERRED EMBODIMENTS

Hereinafter, the present invention will be described in detail by way of illustrating examples with reference to FIGS. 1(a) to 8.

Figure 1A:
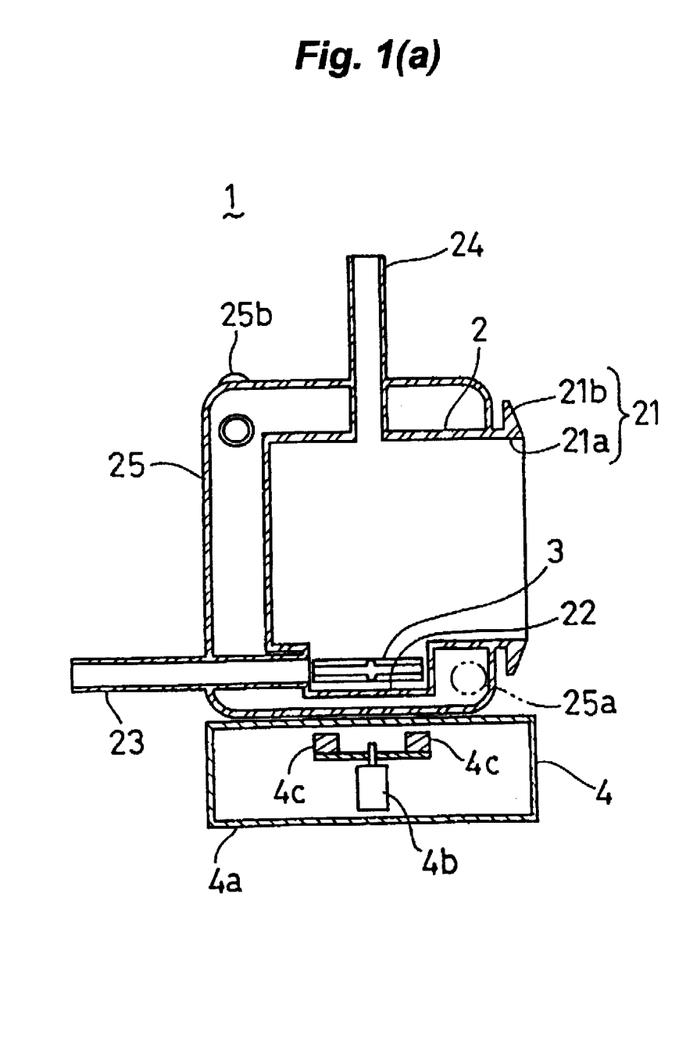
Figure 1B:
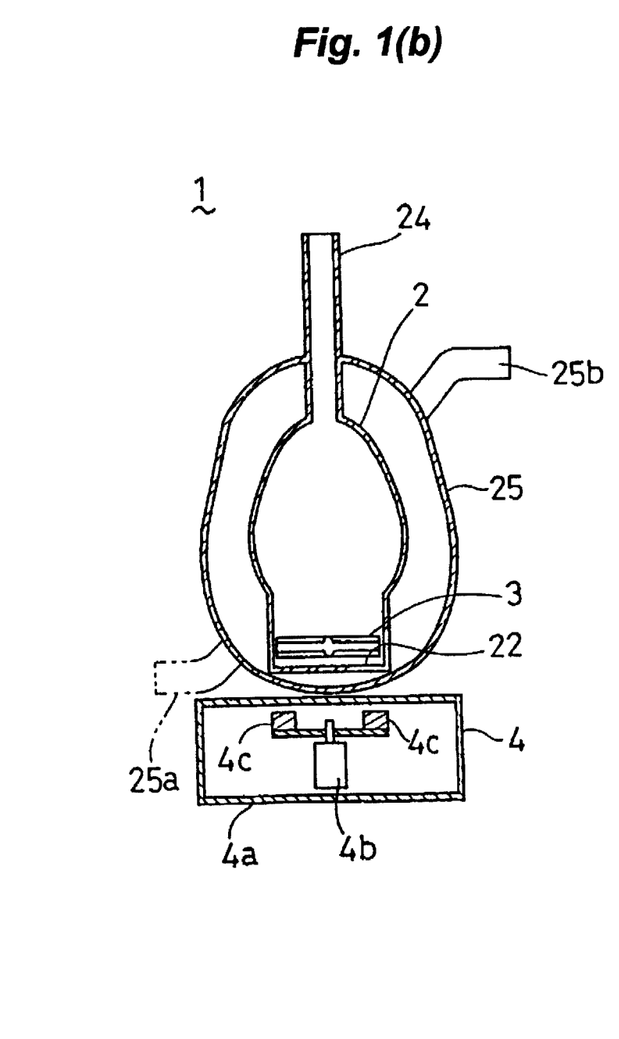
Figure 2:
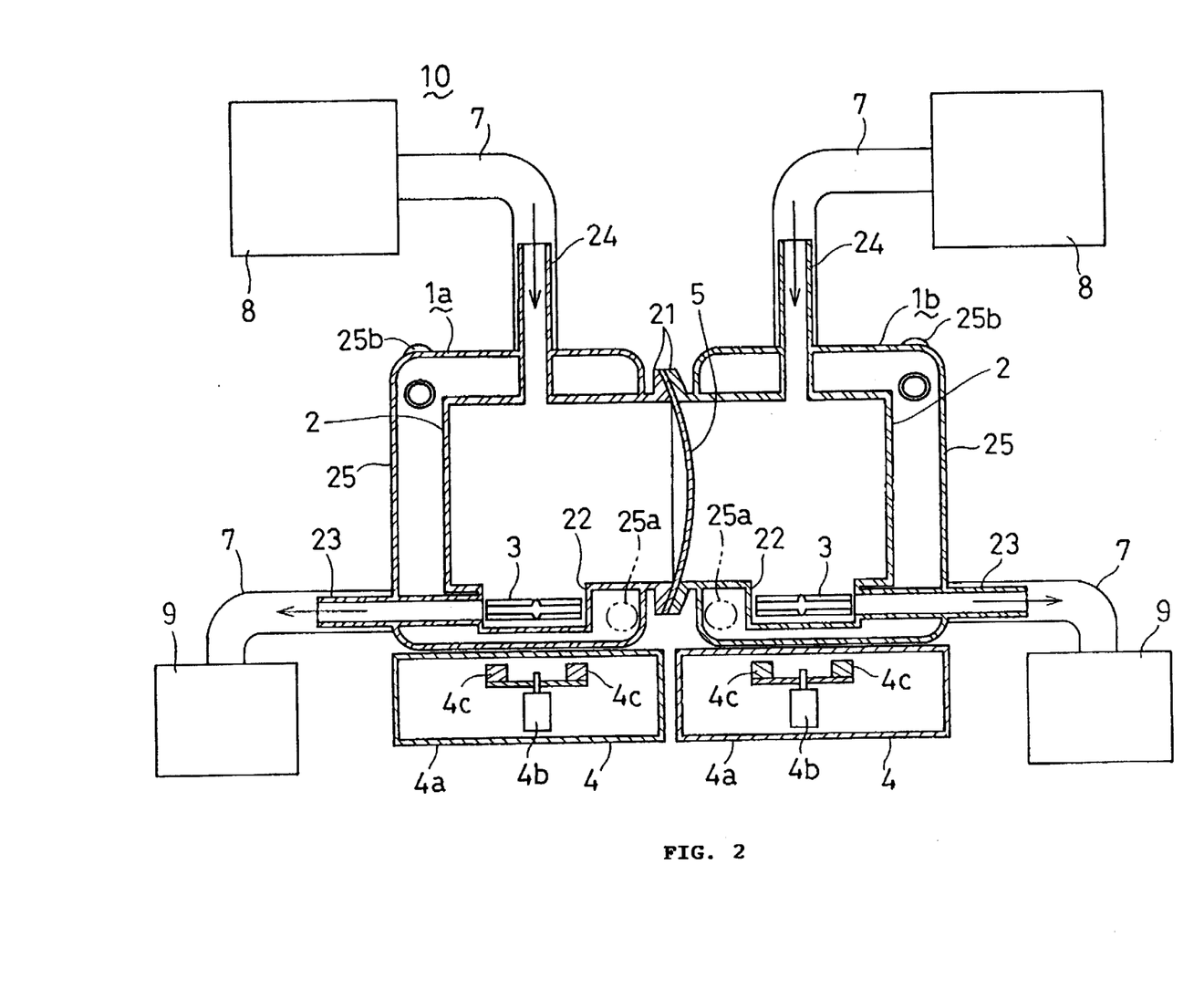
FIG. 2 is a schematic view for exemplarily illustrating a general structure of an open type of experimental unit for examining permeability of a flowing cornea according to the present invention.

FIGS. 1(a–b) shows a general structure of an experimental instrument for examining permeability of a flowing cornea according to an example of the present invention. (Hereinafter referred to just a experimental instrument.) FIG. 2 shows a general structure of the open type of experimental unit 10 using the same experimental instrument.

In other words, the experimental instrument 1 comprises a cell body 2, a magnet rotator 3, and a magnet stirrer 4.

Figure 3A:
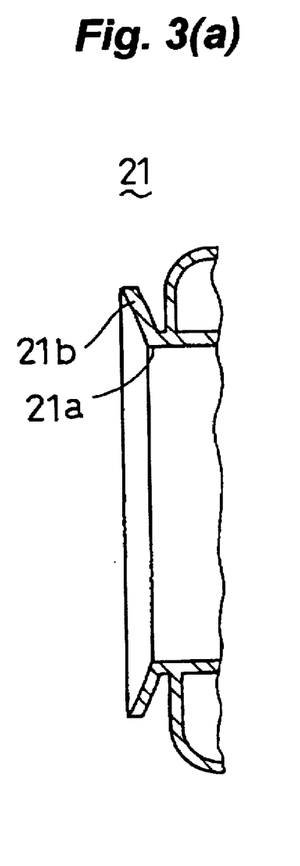
FIG. 3(a) is a fragmentary sectional view illustrating another example in a sample membrane setting part according to the present invention.
Figure 3B:
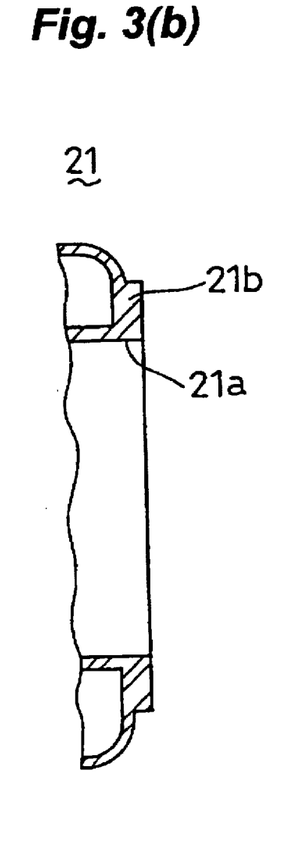
FIG. 3(b) is a fragmentary sectional view illustrating another example in a sample membrane setting part according to the present invention.

The cell body 2 includes an opening 21a on a side, on which the flange face 2b is peripherally arranged, wherein a sample membrane setting part 21 is formed. The sample membrane setting part 21 may be convex spherical-curved surface as shown in FIG. 1 and it may also be the concave spherical-curved surface which can hold a spherical sample membrane 5 such as a contact lens tightly by means of fitting the convex spherical-curved surface as shown in FIG. 3(a). As shown in FIG. 3(b), it may be the flat sample membrane setting part 21 which can hold the plate shaped sample membrane 5 tightly.

At a bottom of the cell body 2, a stirring part 22 having a cylindrical wall and a bottom surface is arranged recessively so as to rotate a magnet rotator 3. The peripheral surface of the stirring part 22 is protrusively provided with an outflow tube 23 for discharging a solution in the cell body 2. In other words, the magnet rotator 3 causes a swirling flow in the stirring part 22, whereby the solution in the cell body 2 can be discharged from the outflow tube 23. The stirring part 22 is arranged recessively at the bottom of the cell body 2 to prevent a swirling flow from influencing directly the sample membrane setting part 21, thereby obtaining the calm flow of a solution in the cell body 2.

On an upper part of the cell body 2, an inflow tube 24 is protrusively arranged, which makes the solution flow into the cell body 2.

The cell body 2 is wholly surrounded by a water jacket 25 including an inlet 25a of a constant temperature circulation liquid and an outlet 25b of a constant temperature circulation liquid, through which the cell body 2 can circulate the constant temperature circulation liquid. The constant temperature circulation liquid enables the solution in the cell body 2 to be controlled at the desired temperature.

The cell body 2 having the above structure can be made of a material such as glass and acrylic-polyester in which the absorption of medicines is a very small quantity. The capacity is not fixed, which is adapted in view of the flowing volume and the sampling volume of a solution. Usually, 3.5 to 15 ml is the appropriate extension.

Figure 4A:
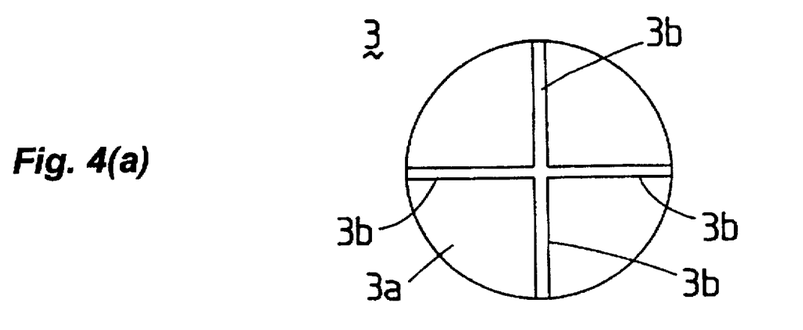
FIG. 4(a) is a plan view showing a magnet rotator according to an example of the present invention.
Figure 4B:
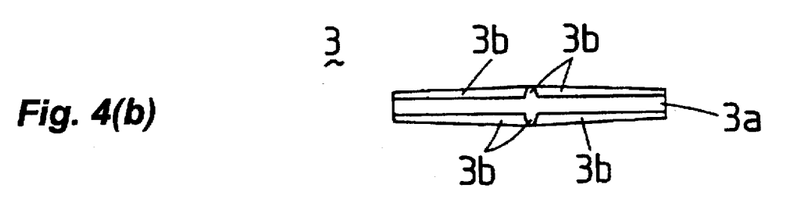
FIG. 4(b) is a side view showing the magnet rotator of FIG. 4(a).
Figure 5A:
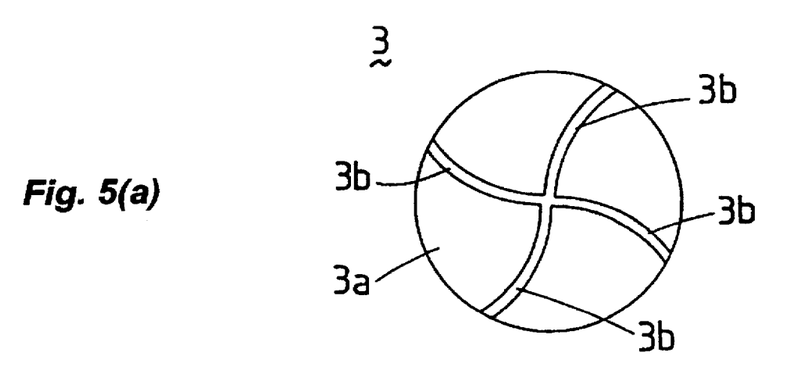
FIG. 5(a) is a plan view showing a magnet rotator according to another example of the present invention.
Figure 5B:
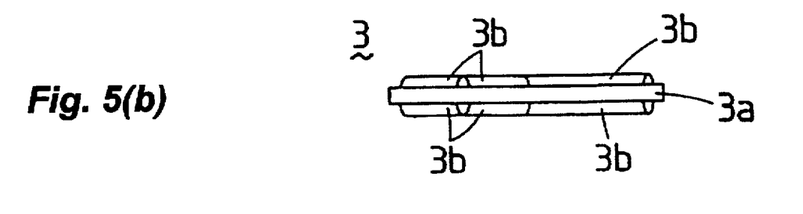
FIG. 5(b) is a side view showing the magnet rotator of FIG. 5(a).

As shown in FIG. 4, the magnet rotator 3 includes a disc-like base 3a and blade parts 3b. The blade part 3b is formed on either side of the base 3a so as to have a cross-shape in a plan view. By means of rotating the blade parts 3b in the stirring part 22 of the cell body 2, the solution in the cell body 2 can be swirlingly circulated quickly. The magnet rotator 3 has a slightly protruding portion at a crossing portion of the blade part 3b formed on either side thereof. During the rotation, the protruding portion becomes a center of the rotation, and therefore the magnet rotator 3 can be rotated stably. This magnet rotator 3 has a structure in which a metal material or a magnet is covered with heat resisting and chemical resisting plastic resin such as Teflon (TM). It is needless to say that the shape of the magnet rotator 3 is not limited to that of a crossing shape in a plan view and each blade part, but it may have any shape as long as the solution in the stirring part 22 of the cell body 2 can be swirlingly circulated by means of the rotation of the magnet rotator 3. For example, the blade part 36 may have a plurality of arc-shaped portions as shown in FIG. 5. Alternatively, a bar-like magnet rotator to be used in a general stirring apparatus (not shown) may be employed as the magnet rotator 3 of the present invention.

As the magnet stirrer 4 of the present invention, a magnet stirrer to be used in a general stirring apparatus may be employed. As shown in FIG. 1, the magnet stirrer 4 includes a stirrer body 4a, a motor 4b, and magnets 4c to be rotated by the motor 4b. The speed of revolution of each magnet 4c can be controlled by adjusting a controller (not shown). With the thus controlled magnets 4c, the magnet rotator 3 in the cell body 2 located on a top surface of the magnet stirrer 4 can be rotated at desired speed of revolution.

Figure 6:
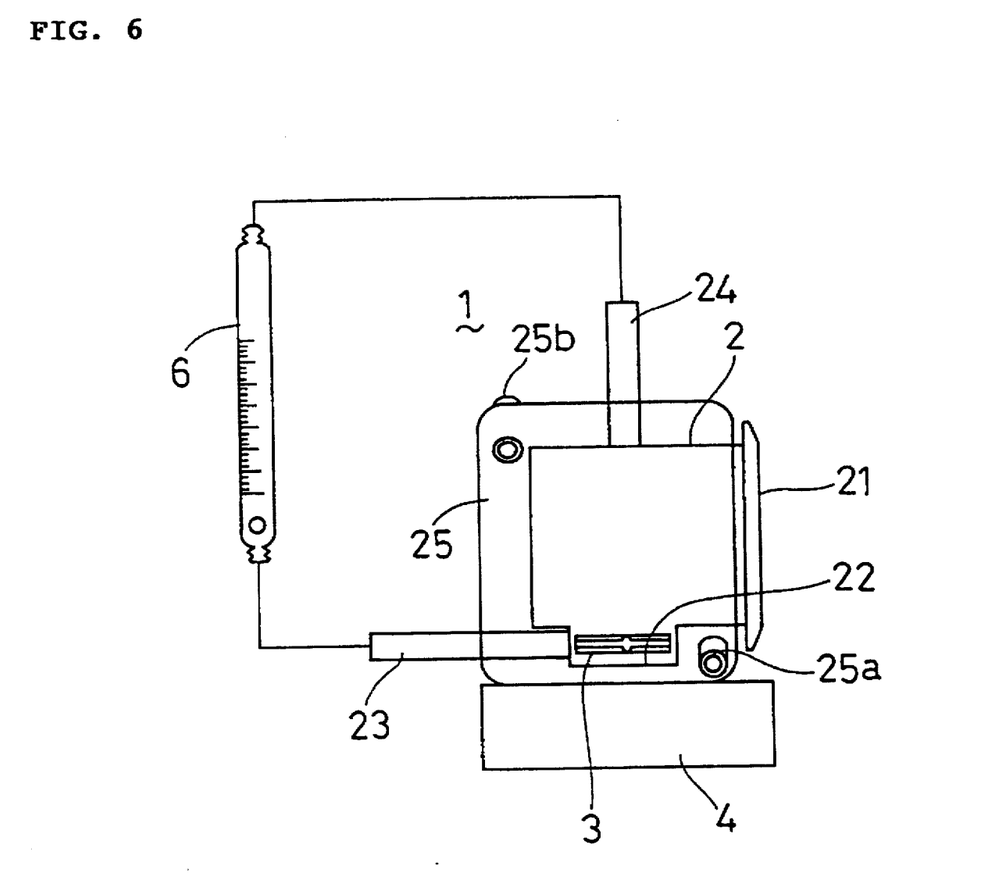
FIG. 6 is a schematic view for exemplarily illustrating a method for measuring volume of flow by means of the experimental instrument for examining permeability of a flowing cornea of the present invention.

The thus obtained experimental instrument 1 is required to determine a relationship between the number of revolution of the magnet rotator 3 and the volume of flow of the solution discharged from the cell body 2 in a prescribed period of time prior to use. To determine the relationship, the sample membrane setting part 21 is in a closed state, a flow meter 6 is arranged between the outflow tube 23 and the inflow tube 24 of the experimental instrument 1 so as to circulate the solution, as shown in FIG. 6. Next, the magnet rotator 3 is rotated at various numbers of revolution per minute by controlling the magnet stirrer 4, while graduations on the flow meter 6 are read for each number of revolution. Finally using an analytical curve attached to the flow meter 6, volume of flow of the solution for each number of revolution can be obtained. Generally, a flow meter is provided with analytical curves with respect to various gases and liquids in purchase. For a case where an analytical curve is not provided for the solution to be measured, a method for obtaining the analytical curve will be described in addition. First, some volume of the solution is put into the flow meter 6 and graduations on the flow meter 6 are read at that time. Then, the volume of the solution is measured using a measuring cylinder or the like. This procedure is repeated with several different graduations on the flow meter 6, thereby obtaining the analytical curve for the solution.

The relationship between the number of revolution of the magnet rotator 3 and the volume of flow of the solution is thus determined in the experimental instruments 1 which is connected to each sample membrane setting part 21 of 2 sets of the experimental instruments via the sample membrane 5 such as a contact lens as the cornea or the corneal model. In the experimental unit 10, the outflow tube 23 and the inflow tube 24 are respectively connected to a container 8 and an analyzing equipment 9 or the like by means of pipe via tubes 7 made of a heat resisting and chemical resisting material such as Teflon (TM) to be constructed as the open typed experimental unit 10 for experimental use.

Next, an embodiment of the experimental method according to the open type of experimental unit 10 is described.

Previous to the experiment, one experimental instrument 1 is referred a donor cell 1a, the other experimental instrument 1 is a receptor cell 1b. In order to make the inside of the donor cell 1a become the state of the lacrimal layer in the front part of a cornea immediately after applying eye drops to eyes, a solution of lacrimal fluid including the eye drops is stored in the inside of the donor cell 1a. On the other hand, the inside of the receptor cell 1b stores a solution equal to the aqueous humor of the back part of the cornea.

Then, the inflow tube 24 in the donor cell 1a is connected with a container 8 which stores a solution composing of only the lacrimal fluid which does not have eye drops. By means of rotation of the magnet rotator 3, the lacrimal fluid in the container 8 is fed to the inside of the donor cell 1a to be discharged from the outflow tube 23, which is periodically sampled and analyzed at the analyzing equipment 9. At that time, the experimental unit 1 controls the swirling flow which happens in the cell body 2 by means of changing the number of revolution of the magnet rotator 3, with the result that the solution of the lacrimal fluid which does not include the eye drops can be continuously supplied at the desired volume of flow. As the result of it, the density of the eye drops in the donor cell 1a can be freely diluted by the zero-degree, the linear or quadratic speed formula, wherein, after applying eye drops, the lachrymal gland secretes the lacrimal fluid, thereby enabling the state of the lacrimal layer of the front part of the cornea in which the eye drops can be diluted to be imitated appropriately.

The container 8 is connected to the inflow tube 24 in the receptor cell 1b, wherein the solution assumed as the same aqueous humor as one in the receptor cell 1b is stored, and the rotation of the magnet rotator 3 causes to supply the inside of the receptor cell 1b with the aqueous humor and periodically sampling the liquid discharged from the outflow tube 23 to analyze it at the analyzing equipment. In this case, it can imitate appropriately a flow of the aqueous humor of the back part of the cornea in the receptor cell 1b.

The donor cell 1a and the receptor cell 1b are connected by the analyzing device 9 which can lead to the result of analyses with passage of time, whereby the behavior of the eye drops in a various kinds of sample membrane 5 can be measured.

According to an experimental unit 10, each experimental unit 1 works owing to the rotation of the magnet rotator 3 by the magnet force. Therefore, the cell body 2 is made of glass and the magnet rotator 3 is covered with Teflon (TM) or the like, whereby a whole of the experimental unit 10 can be superior in heat resisting and chemical resisting. Each experimental unit 1 functions as a pump, wherein it is not necessary to connect the experimental unit 1 with the additional pump. As the result, the mechanical sealing part where there is a fear of a leak of liquid and the elastic tube body where there is a fear of the solution absorption and dissolution can be excluded and the tube ways connected with each experimental instrument 1 are minimized, whereby the balance error can be extremely a little in the experimental unit 10.

In case of being constructed as the experimental unit 10 as mentioned above, in each experimental instrument 1 the relationship between the number of revolution of the magnet rotator 3 and the volume of the flow of the solution is likely to unstable due to the length of the tube body 7, the resistance generated when the solution is fed through the tube body 7, the height where the experimental instrument 1 is arranged and the kind and the volume of the solution in the experimental instrument 1. Therefore, it is preferable to incorporate the flow meter 6 into the experimental instrument 1 (if such incorporation will not raise any trouble in the experimental instrument 1) and control the volume of flow of the solution using the flow meter 6. In this case, the flow controlling ability is easily adaptable by means of design modification of the volume of the cell body 2 and shape, the aperture diameters of the outflow tube 23 and the inflow tube 24 and the shape of the blade part 3b of the magnet rotator 3 or the like.

Figure 7:
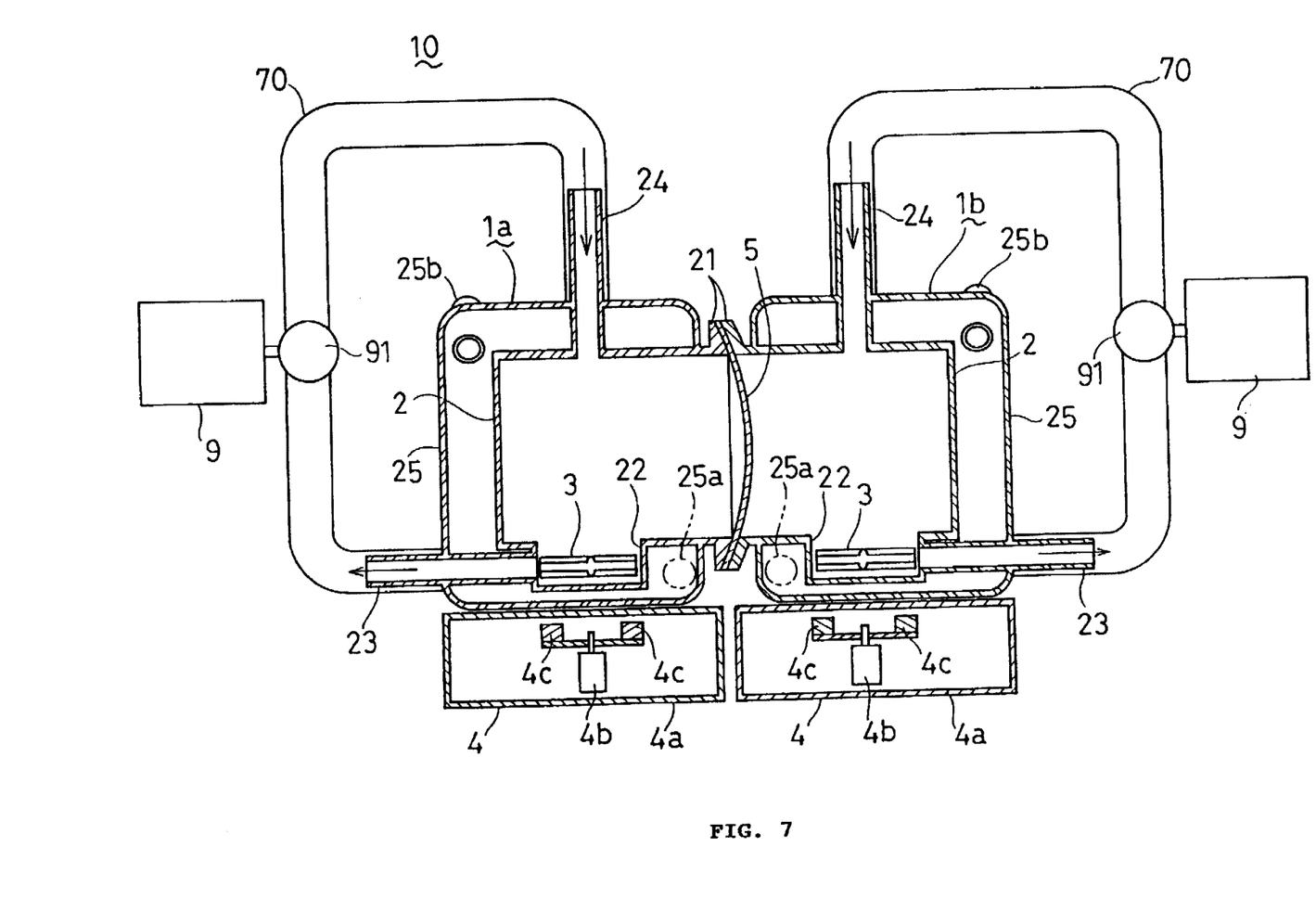
FIG. 7 is a schematic view illustrating a close circulation type of experimental unit, or another example of the experimental unit for examining permeability of a flowing cornea according to the present invention.
Figure 8:
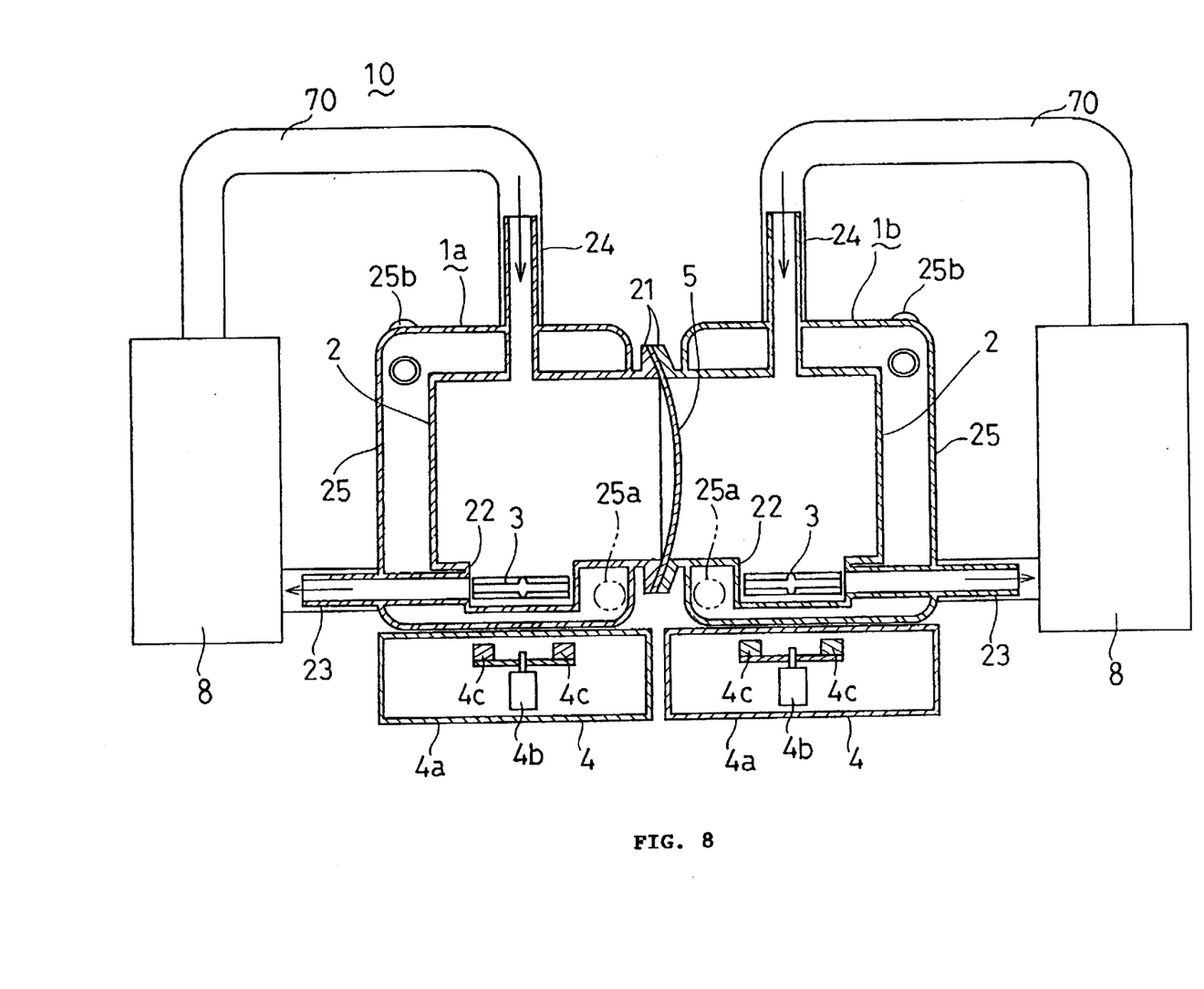
FIG. 8 is a schematic view illustrating an open circulation type experimental unit, or another example of the experimental unit for examining permeability of a flowing cornea according to the present invention.

In this embodiment, the open type of experimental unit 10 is described, but it is needless to say that it is not limited to the open type of one. For example, as shown in FIG. 7, both of the donor cell 1a and the receptor 1b include respectively a close-circulation type tube way 70 which is formed between the outflow tube 23 and the inflow tube 24, wherein the tube way 70 is connected to the analytical equipments 9 such as the high-speed liquid chromatography and the spectrophotometer through an sampling unit 91 with the result that it may be the close circulation type of experimental unit 10. As shown in FIG. 8, both of the donor cell 1a and the receptor 1b include respectively the tube way 70 through which the outflow tube 23 and the inflow tube 24 is connected to an open type of container 8 with the result that it may be the open circulation type of experimental unit 10 wherein the medical solution can be injected from the container 8, and the solution can be sampled. Moreover, it is not necessary for both of the donor cell 1a and the receptor cell 1b to be experimental unit 10 of the same type each other. In other words, the donor cell may be the open type and the receptor cell 1b is the close-circulation type, wherein the experimental unit 10 may be allowed.

What is claimed is:

1. An experimental instrument for examining permeability of a flowing cornea being suited for imitating a lacrimal layer in the front part of a cornea or the back part of the cornea (an aqueous humor) by means of storing a various kinds of solution comprising:

a cell body including a stirring part of a cylindrical wall and a bottom surface at a bottom part thereof, a constant temperature tank which surrounds the cell body all around a sample membrane setting part which is protrusively arranged at an outer surface of the cell body and can set a sample membrane including a contact lens used as a cornea model, an outflow tube which is protrusively arranged at an outer surface of the stirring part and makes a solution in the cell body discharge, an inflow tube which is protrusively arranged at an upper part of the cell body and makes the solution flow inside of the cell body, a magnet rotator which is arranged inside the stirring part of the cell body, and a magnet stirrer which makes the magnet rotator inside the cell body rotate by means of magnetic force.

2. An experimental instrument for examining permeability of a flowing cornea according to claim 1, wherein the sample membrane setting part is formed in the shape of a convex or concave spherical-curved surface which can hold the spherical sample membrane tightly by means of fitting the convex spherical-curved surface.

3. An experimental instrument for examining permeability of a flowing cornea according to claim 1, wherein the stirring part includes a recess formed by means of swelling the bottom of the cell body outwardly.

4. An experimental instrument for examining permeability of a flowing cornea according to claim 1, wherein the magnet rotator includes a disk-like base, and a blade part formed on either side of the base so as to have a cross-shape in a plan view and have a protruding portion at a crossing portion thereof.

5. An experimental instrument for examining permeability of a flowing cornea according to claim 1, wherein the magnet rotator includes a disk-like base, and a blade part formed on either side of the base so as to have a plurality of arc-shaped portions.

6. An experimental instrument for examining permeability of a flowing cornea according to claim 4, wherein the magnet rotator is covered with heat resisting and chemical resisting synthetic resin.

7. An experimental instrument for examining permeability of a flowing cornea according to claim 5, wherein the magnet rotator is covered with heat resisting and chemical resisting synthetic resin.

8. An experimental unit for examining permeability of a flowing cornea comprising:

two sets of experimental instruments for examining permeability of a flowing cornea, and each of the experimental instruments having:

a cell body including a stirring part of a cylindrical wall and a bottom surface at a bottom part thereof, a constant temperature tank which surrounds the cell body all around a sample membrane setting part which is protrusively arranged at an outer surface of the cell body and can set a sample membrane including a contact lens used as a cornea model, an outflow tube which is protrusively arranged at an outer surface of the stirring part and makes a solution in the cell body discharge, an inflow tube which is protrusively arranged at an upper part of the cell body and makes the solution flow inside of the cell body, a magnet rotator which is arranged inside the stirring part of the cell body, and a magnet stirrer which makes the magnet rotator inside the cell body rotate by means of magnetic force, wherein the two sets of the experimental instruments are structurally connected with each other through the sample membrane including a contact lens used as a cornea model set between the sample membrane setting parts.

* * * * *